United States Patent [19]

MacLean et al.

[11] Patent Number: 5,719,190

[45] Date of Patent: Feb. 17, 1998

[54] INHIBITION OF MYELOPEROXIDASE ACTIVITY

[75] Inventors: David B. MacLean, Providence, R.I.; David D. Thompson, Gales Ferry, Conn.

[73] Assignee: Pfizer Inc., New York, N.Y.

[21] Appl. No.: 803,709

[22] Filed: Feb. 21, 1997

[51] Int. Cl.$^6$ .................................................. A61K 31/135
[52] U.S. Cl. ............................................................ 514/648
[58] Field of Search ............................................. 514/648

[56] References Cited

U.S. PATENT DOCUMENTS

| | | |
|---|---|---|
| 5,047,431 | 9/1991 | Schickaneder et al. ............... 514/648 |
| 5,254,594 | 10/1993 | Kazuaki et al. ...................... 514/648 |
| 5,384,332 | 1/1995 | Fontana ................................ 514/648 |
| 5,441,986 | 8/1995 | Thompson ............................ 514/648 |
| 5,455,275 | 10/1995 | Fontana ................................ 514/648 |
| 5,550,164 | 8/1996 | Fontana ................................ 514/648 |

FOREIGN PATENT DOCUMENTS 0664125  7/1995  European Pat. Off. ..... A61K 31/445

Primary Examiner—Jerome D. Goldberg

Attorney, Agent, or Firm—Peter C. Richardson; Gregg C. Benson; Mervin E. Brokke

[57] ABSTRACT

The present invention provides novel methods of inhibiting myeloperoxidase activity comprising administering to a mammal in need of such treatment an effective amount of a compound of formula I

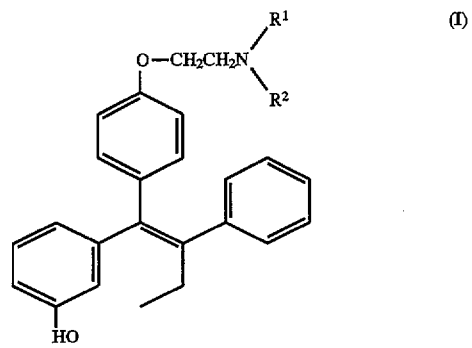

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

3 Claims, No Drawings

INHIBITION OF MYELOPEROXIDASE ACTIVITY

This is a continuation of provisional application 60/012,403 filed Feb. 28, 1986, the benefit of which is hereby claimed under 37 C.F.R. §1.78(a)(3).

BACKGROUND OF THE INVENTION

Autoimmune diseases involve aberrant regulation of cellular and humoral mediated immunity and are frequently associated with abnormal or enhanced T cell, B cell and macrophage effector functions directed towards self antigens. The activation of these cellular components towards self antigens is believed related to the break in feedback mechanisms associated with self tolerance. Autoimmune diseases encompass a whole spectrum of clinical entities and despite the differences in the target organ have many similarities. These include their preponderance in females of child bearing age with a female to male ratio varying from 50:1 in Hashimoto's thyroiditis to 10:1 in Systemic lupus erythematosus (SLE) to 2:1 in *Myasthenia gravis* (Ahmed et al., Am J. Path., 121:531 (1985)). In addition, these diseases are all characterized by the chronicity, the tendency of clinical remission and "flare ups" for poorly understood reasons, and the involvement of other organs. While the presence of autoantibodies, inappropriate expression of class II antigens, macrophage activation and T cell infiltration to the target organ have been described in essentially all of the autoimmune diseases, neither the triggering mechanisms which result in disease activation not disease progression are well understood. Accordingly, therapy for these diseases is largely unsatisfactory and involves the use of gold salts, methotrexate, antimalarials, glucocorticoids (methylprednisolone), and other immunosuppressives as well as plasmaphoresis and attempts at inducing tolerance. Treatment of autoimmune diseases has not improved significantly over the past decade and primarily is associated with the use of nonsteroidal and steroidal anti-inflammatory agents to treat the symptoms of the disease. Clearly while suppression of the specific immune response directed against the host is necessary, generalized immunosuppression as with glucocorticoids has major liabilities in terms of side effect profile and the propensity of the immunosuppressed patient to be at greater risk for other infectious and non-infectious diseases.

*Polymorphonuclear leukocytes* (PMNL) play a regulatory role in inflammatory diseases. These cells, when activated, synthesize and release oxygen-centered molecules, chemoattractents, and hydrolytic enzymes. There is evidence that the oxygen-centered molecules play a detrimental role in a number of diseases such as chronic inflammatory diseases, rheumatoid arthritis, SLE, and others. In the case of an autoimmune disease, SLE, for example, the initiation of an inflammatory response are self antigen stimulating one's host neutrophils or PMNLs to secrete strong oxidants which damage surrounding cells and tissue.

Estrogen appears to be involved with autoimmune diseases although its role in disease progression or regression is complex and dependent on the nature of the autoimmune disease. Estrogen for example appears to have ameliorating effect on rheumatoid arthritis while having an exacerbating effect on systemic lupus (Chander & Spector; Ann. Rheum. Dis. 50:139). As reported by Jansson (*Free Rad Res Comms*, 14(3), 195–208, (1991), incorporated herein by reference), estrogen increased the activity of an enzyme generated by PMNLs, myeloperoxidase, which regulates the production of oxidants from hydrogen peroxide. This enzyme converts hydrogen peroxide to hypochlorous acid, a strong oxidant. By increasing the enzyme's activity, and thus the presence of hypochlorous acid, the likelihood of increased oxidative stress on tissues, cells and various macromolecules in chronic inflammatory/autoimmune diseases is enhanced.

EP 664 125 A1 reports that inhibition of myeloperoxidase may be accomplished by treatment with certain 3-aroyl benzothiophines. Excess myeloperoxidase is associated with conditions which include systemic lupus erythematosis, Hashimoto's thyroiditis, myasthenia gravis, rheumatoid arthritis and multiple sclerosis.

SUMMARY OF THE INVENTION

The present invention relates to methods for inhibiting myeloperoxidase activity comprising administering to a mammal in need of treatment an effective amount of a compound of formula I

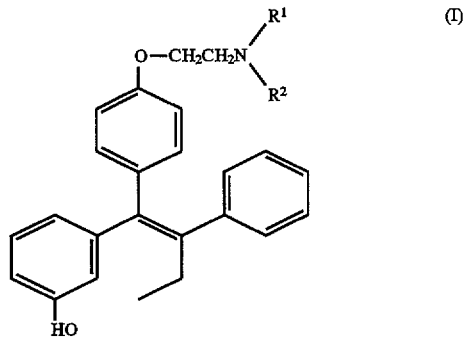

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen a benzyl group; or a pharmaceutically acceptable salt thereof. A preferred compound of formula I is that in which $R^1$ and $R^2$ are methyl. A preferred salt is the citrate salt.

DETAILED DESCRIPTION OF THE INVENTION

The present invention concerns methods for inhibiting myeloperoxidase activity and thus provides utility in the treatment of autoimmune and chronic inflammatory diseases. The "term inhibit" is defined to include its generally accepted meaning which includes prophylactically treating a subject to prevent the occurrence of one or more of these disease states, holding in check the symptoms of such a disease state, and/or treating such symptoms. Thus, the present methods include both medical therapeutic and/or prophylactic treatment, as appropriate.

The methods of this invention are practiced by administering to a mammal in need of treatment an effective amount of a compound formula I

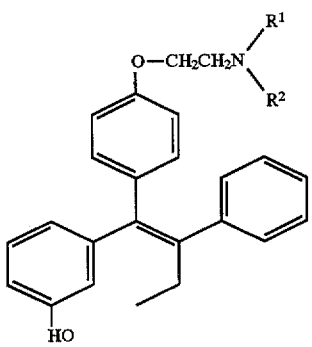

(I)

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a benzyl group or a pharmaceutically acceptable salt thereof.

Compounds of formula I are known in the art and essentially are prepared via the methods described in U.S. Pat. No. 5,047,431, which is hereby incorporated herein by reference.

A preferred formula I compound is that in which $R^1$ and $R^2$ each are methyl. This preferred compound is known as droloxifene, (E)-1-[4'-(2-Dimethylaminoethoxy)phenyl]-1-(3-hydroxyphenyl)-2-phenylbut-1-ene, which previously has been described as an antiestrogentc agent and is useful for the treatment of hormone dependent mammary tumors (U.S. Pat. No. 5,047,431), and for the relief of bone diseases caused by the deficiency of estrogen or the like (U.S. Pat. No. 5,254,594). Furthermore, droloxifene is known to have less uterotrophic effect than other antiestrogenic compounds such as tamoxifen.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate,β-hydroxybutyrate, butyne-1,4-dioate, hexyne-1,4-diote, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the methods herein described. The following nonlimiting test examples illustrate the methods of the present invention.

For the methods of the present invention, compounds of Formula I are administered continuously, or from 1 to 4 times daily.

As used herein, the term "effective amount" means an amount of compound of the methods of the present invention which is capable of inhibiting the symptoms of the pathological conditions herein described. The specific dose of a compound administered according to this invention will, of course, be determined by the particular circumstances surrounding the case including, for example, the compound administered, the route of administration, the state of being of the patient, and the severity of the pathological condition being treated. A typical daily dose will contain a nontoxic dosage level of from about 0.25 mg to about 100 mg/day of a compound of the present invention. Preferred daily doses generally will be from about 1 mg to about 40 mg/day.

The compounds of this invention can be administered by a variety of routes including oral, rectal, transdermal, subucutaneous, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannltol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

In the formulations which follow, "active ingredient" means a compound of formula I, or a salt thereof.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredient are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of medicament per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The medicament is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool. An intravenous formulation is prepared as follows:

Formulation 7: Intravenous Solution

| Ingredient | Quantity |
| --- | --- |
| Active ingredient | 20 mg |
| Isotonic saline | 1,000 mL |

The solution of the above ingredients is intravenously administered to a patient at a rate of about 1 mL per minute, Assay 1

In order to investigate the myeloperoxidase activity inhibiting properties of compounds of formula 1, Assays 1 and 2, as set out in Jansson (supra.), are employed.

In this assay, human PMN leukocytes are stimulated with estriol to increase myeloperoxidase activity in the presence of added hydrogen peroxide. The conversion of luminol by hypochlorous acid is measured by chemiluminescence. The reaction mix consists of cells ($10^6$) agent or compound of formula 1 (1 μM), hydrogen peroxide (0.1 mM), and luminol (0.2 mM) incubated at 37° C.

Estrogen and its analogs stimulate myeloperoxidase activity. Compounds of formula 1 antagonize the estriol stimulated chemiluminescence.

Assay 2

Purified human myeloperoxidase is incubated with agent (estrogen or a compound of formula 1 ), in the presence of luminol at 37° C. The substrate, hydrogen peroxide, is added and the chemiluminescence measured. The reaction mix is human MPE (250 ng), agent or a compound of formula I (10 μM, titrated), hydrogen peroxide (1 mm), and luminol (0.2 mm).

Estrogen and its analogs have little or no effect on MPE activity, however, compounds of formula 1 reduce the activity of purified MPE.

ASSAY 3

Five to fifty women are selected for the clinical study. The women suffer from SLE or rheumatoid arthritis. Because of the idiosyncratic and subjective nature of these disorders, the study has a placebo control group, i.e., the women are divided into two groups, one of which receives a compound of formula I as the active agent and the other receives a placebo. Women in the test group receive between 50–100 mg of the drug per day by the oral route. They continue this therapy for 3–12 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula 1 is illustrated by the positive impact they have in at least one of the assays described above.

We claim:

1. A method of (inhibiting myeloperoxidase activity) treating systemic lupus erythematosis, Hashimoto's thyroiditis, myasthenia gravis, rheumatoid arthritis and multiple sclerosis comprising administering to a mammal in need of (such) said treatment an effective amount of a compound of formula I

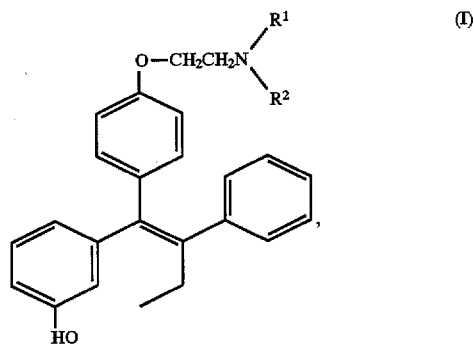

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or (a) benzyl (group); or a pharmaceutically acceptable salt thereof.

2. A method according to claim 1 wherein the compound of formula I is a compound wherein $R^1$ and $R^2$ each are methyl, or a pharmaceutically acceptable salt thereof.

3. A method according to claim 2 wherein said salt thereof is the citrate salt.

* * * * *